(12) United States Patent
Cewers

(10) Patent No.: US 7,870,858 B2
(45) Date of Patent: Jan. 18, 2011

(54) APPARATUS AND METHOD FOR DRIVING A SENSOR IN A VENTILATOR

(75) Inventor: Göran Cewers, Limhamn (SE)

(73) Assignee: RIC Investments, LLC, Wilmington, DE (US)

( * ) Notice: Subject to any disclaimer, the term of this patent is extended or adjusted under 35 U.S.C. 154(b) by 757 days.

(21) Appl. No.: 11/574,373

(22) PCT Filed: Sep. 1, 2005

(86) PCT No.: PCT/EP2005/009437

§ 371 (c)(1),
(2), (4) Date: Oct. 22, 2007

(87) PCT Pub. No.: WO2006/024531

PCT Pub. Date: Mar. 9, 2006

(65) Prior Publication Data

US 2008/0121232 A1    May 29, 2008

(30) Foreign Application Priority Data

Sep. 3, 2004    (SE) .................................... 0402119

(51) Int. Cl.
*A61M 11/00*    (2006.01)
(52) U.S. Cl. ............................ 128/204.22; 128/204.21; 128/204.23
(58) Field of Classification Search ............ 128/204.18, 128/204.21, 204.22, 204.23, 204.26
See application file for complete search history.

(56) References Cited

U.S. PATENT DOCUMENTS

| 3,033,195 A | 5/1962 | Gilroy et al. |
| 3,358,511 A | 12/1967 | Bargen |
| 3,831,596 A | 8/1974 | Cavallo |
| 5,845,636 A * | 12/1998 | Gruenke et al. ........ 128/204.23 |

FOREIGN PATENT DOCUMENTS

| EP | 0968734 | 1/2000 |
| EP | 1205200 | 5/2002 |

* cited by examiner

*Primary Examiner*—Steven O Douglas

(57) ABSTRACT

A ventilator includes a sensor to monitor a characteristic associated with the delivery of gas to the patient, such as pressure. A sensor power supply (100, 130) is feeding a sensor in the form of a Wheatstone bridge. A first end (104) of the bridge is coupled to a first positive voltage source (112, 142) and a second end (116) is coupled to a second positive voltage source (118, 156, 180). A capacitor (120) is coupled to the second end of the bridge. A controller (50) controls the first and the second positive voltage sources so as to (a) disable the sensor by causing the first positive voltage source to provide substantially zero voltage to the first end of the Wheatstone bridge and by causing the second positive voltage source to provide a positive voltage to the second end of the capacitor, and to (b) enable the sensor by causing the first positive voltage source to provide a positive voltage to the first end of the Wheatstone bridge and by causing the second positive voltage source to provide a decreasing voltage to the second end of the capacitor.

15 Claims, 5 Drawing Sheets

APPARATUS AND METHOD FOR DRIVING A SENSOR IN A VENTILATOR

PRIORITY CLAIM

This application claims priority from Swedish Patent Application Serial No. 0402119-2 filed Sep. 3, 2004.

TECHNICAL FIELD

The present invention pertains to a technique for providing power to one or more sensors in a ventilator, and, in particular, to a sensor system that maintains the sensor in a disabled state until a measurement is needed, in which point the sensor is quickly and temporarily switched to an enabled state so that the measurement can be taken.

BACKGROUND OF THE INVENTION

It is well known to utilize a ventilator, anesthesia machine, or pressure support device or other system to deliver a fluid, such as oxygen, air, or other breathing gas or gas mixture, to an airway of patient to augment, supplement, or substitute the patient's own ventilatory effort and/or to treat the patient with a pressure support therapy. Of importance in using such situations is the ability to accurately regulate or control the pressure, flow, and/or volume of gas delivered to the patient. This requires being able to accurately monitor the operating parameters of the ventilator, such as the pressure and/or flow of gas in the ventilator. For present purposes, the term "ventilator" is used to describe any system or device that delivers a flow of gas or pressurized gas to the airway of a user, either invasively or non-invasively, alone or in combination with other systems.

As shown in FIG. 1, the inspiratory related components of a conventional ventilator 20 includes a source of a first gas 30, such as air, and a source of a second gas 32, such as oxygen. The source of first gas typically includes a pressurized storage tank, blower, bellows, impeller, fan, piston, pressure generator, or the like, that provides pressured air at a pressure above ambient pressure. The source of oxygen is typically a pressurized oxygen storage tank, a central wall supply (typically found in a hospital), or an oxygen concentrator. In short, the sources of the first and second gas can be pressure generators that operate under the control of the ventilator, an independent gas supply, such as that available through a hospital's central gas delivery system, or a combination thereof.

A first valve 34 control the supply of the first gas (e.g., air) and a second valve 36 controls the supply of the second gas (e.g., oxygen). The separate gas supplies are mixed downstream of the valves, typically using a mixing element or accumulator, for subsequent delivery to the patient via the inspiratory limb of a patient circuit. The combined gas flow is carried by a primary conduit 42 to an external coupling provided on the ventilator housing. A flexible hose or patient circuit (not shown) couples to the external coupling an airway of the patient. Valves 34 and 36 are typically proportional valves the are opened or closed based on the direction that current flow through the valve, which is a function of the voltage applied across the valve.

The illustrated conventional ventilator includes a first flow sensor 44 adapted to measure a flow of the first gas and a second flow sensor 46 adapted to measure the flow of the second gas. A pressure sensor 48 measures the pressure of the gas in conduit 42 delivered to the patient via the patient circuit. In addition, and oxygen concentration monitor 49 measure the concentration of oxygen in the gas delivered to the patient. The outputs of flow sensors 44 and 46, pressure sensor 48, and oxygen monitor 49 are provided to a controller 50. The controller typically uses this information, at least in some ventilation modes, to control the flow, volume, and/or pressure of gas delivered to the patient, i.e., to control valves 34 and 30 and/or the actuation of the gas sources 30 and/or 32 so that the desired flow, pressure, or volume of gas is administered to the patient having the desired oxygen concentration.

The expiratory components of a conventional ventilator include a expiratory conduit 60 that is coupled to the expiratory limb of the patient circuit. In a conventional setup, the inspiratory limb and the expiratory limb are coupled near the patient at a Y-connector (not shown). The expiratory limb carries gas from the patient back to the ventilator. An expiratory valve 62 that operates under the control of the controller is coupled to conduit 60 to control the release of gas from the conduit into the atmosphere. Sensor, such as a pressure sensor 64 and/or a flow sensor 66 are provided to measure the pressure and/or flow of gas in the expiratory conduit.

A frequently occurring problem with conventional ventilators is that, when a ventilator has to be attached to a patient in an emergency, the ventilator may have a reduced accuracy during a period of time after the start-up of the ventilator. This period of reduced or impaired operating ability can last as long as half an hour of the treatment is started. This problem is of particular importance when ventilating children, and, in the worst case, the patient can be injured as a consequence of the ventilator delivering incorrect flows and/or pressures to the patient. One reason the ventilator may operate with a reduce or impaired ability at start-up is due to heating-up related phenomena that is inherent in the sensing elements of the ventilator, such as the pressure sensors, flow sensors, oxygen concentration sensors, temperature sensors, that are used to monitor one or more characteristics associated with the flow of the gas delivered to or received from the patient.

Conventional ventilators also typically use multiple electronic components, such as flow regulators (valves), sensors (pressure, flow, gas concentration, temperature), processors, etc, that do not operate at the same voltage or current level, i.e., the valves have different power requirements. FIG. 2 is a schematic representation of a conventional ventilator that includes a common power supply of 12 V. In this example, valves 70 and 72 operate at ±12 V. These valves correspond, for example, to one or more of valves 34, 36, and 62 used in the ventilator of FIG. 1. To provide ±12 V to the valves, switched converters 74 and 76 used to switch the 12 V to be provided to the valve between +12 V and −12 V. Other components of the ventilator have other power requirements. For example, processor or controller 50 operates at a voltage level of 3.3 V. A voltage converter 78 converts the 12 V to 3.3 V for use by the controller. In this example, sensors 82 and 84 operate at voltages of ±5 V. These sensor correspond, for example, to any one of the sensors used in the ventilator, such as flow sensors 44, 46, and 66, pressure sensors 48 and 64, and oxygen sensor 49. Voltage converters 90 and 92 convert the +12 V to +5 V, and inverters 94 and 96 are provided to so that both +5 V and −5 V are available for such sensors. Of course, a single voltage converter and single inverter can be used to provide the ±5 V.

When a ventilator requires multiple voltages, there is a challenge in ensuring that the signal/noise-ratio of the various power supplies is kept to an acceptably low level. This is especially difficult in an environment where switched converters are used, because such components include rapidly actuated switches that can induce voltage spikes and other transient noise in the power supply system. For example, noise in the power supply can interfere with pulse width modulated signals used to control the valves or can interfere with the signals provided by the sensors. In a worst case scenario, the interferences can cause inadvertent actuation or deactivate of a ventilator valve used to control the delivery of gas to the patient.

Another problem with ventilators that require multiple voltages is the fact that each voltage source requires separate testing and monitoring in order ensure that each voltage source is providing the correct voltage within a specified tolerance range. This testing and accuracy especially critical in medical equipment, where a patient's health could be impacted by faulty power supplies. A further problem associated with need to use multiple voltages is that a start-up and shut-down, power must be provided to or removed from the various components of the ventilator in a predetermined must sequence. This is necessary to ensure that the components are not damaged during power on or power off. It can be appreciated that the need to control and/or monitor the sequence in which power is provided to or removed from the electronic components of the ventilator leads to high costs in the design of the ventilator and complicates its operation.

One way of reducing the number of voltages is to generate these voltages internally in the ventilator on a module specifically provided for this task. In certain cases, e.g., when generating negative voltages, some form of switching is required, i.e., inductively or capacitively, which leads to undesired disturbances in the power supplies. As noted above, these undesired disturbances may impair the accuracy of the voltage provided to the various electronic components of the ventilator.

DISCLOSURE OF THE INVENTION

Accordingly, it is an object of the present invention to provide a ventilator that overcomes the shortcomings of conventional ventilators. This object is achieved according to one embodiment of the present invention by providing a ventilator that includes a sensor adapted to monitor a characteristic associated with the delivery of gas to the patient, such as pressure or flow sensor. The sensor is in the form of a Wheatstone bridge in which a first end of the bridge is coupled to a first positive voltage source, and a second end of the bridge is coupled to a second positive voltage source. A capacitor is coupled to the second end of the bridge. A controller controls the first and the second positive voltage sources so as to (a) disable the sensor by causing the first positive voltage source to provide substantially zero voltage to the first end of the Wheatstone bridge and by causing the second positive voltage source to provide a positive voltage to the second end of the capacitor, and to (b) enable the sensor by causing the first positive voltage source to provide a positive voltage to the first end of the Wheatstone bridge and by causing the second positive voltage source to provide a decreasing voltage to the second end of the capacitor.

It is yet another object of the present invention to provide a method that does not suffer from the disadvantages associated with conventional systems. This object is achieved by providing a system and method of a method of providing power to a sensor in a ventilator using the above-described apparatus and technique that includes providing a capacitor having a first end is coupled to the second end of the Wheatstone bridge, disabling the sensor by providing (a) a substantially zero voltage to the first end of the Wheatstone bridge and (b) a positive voltage to the second end of the capacitor; and enabling the sensor by providing (a) a positive voltage to the first end of the Wheatstone bridge and (b) a decreasing voltage to the second end of the capacitor.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BEST MODE(S) FOR CARRYING OUT THE INVENTION

Figure 1:
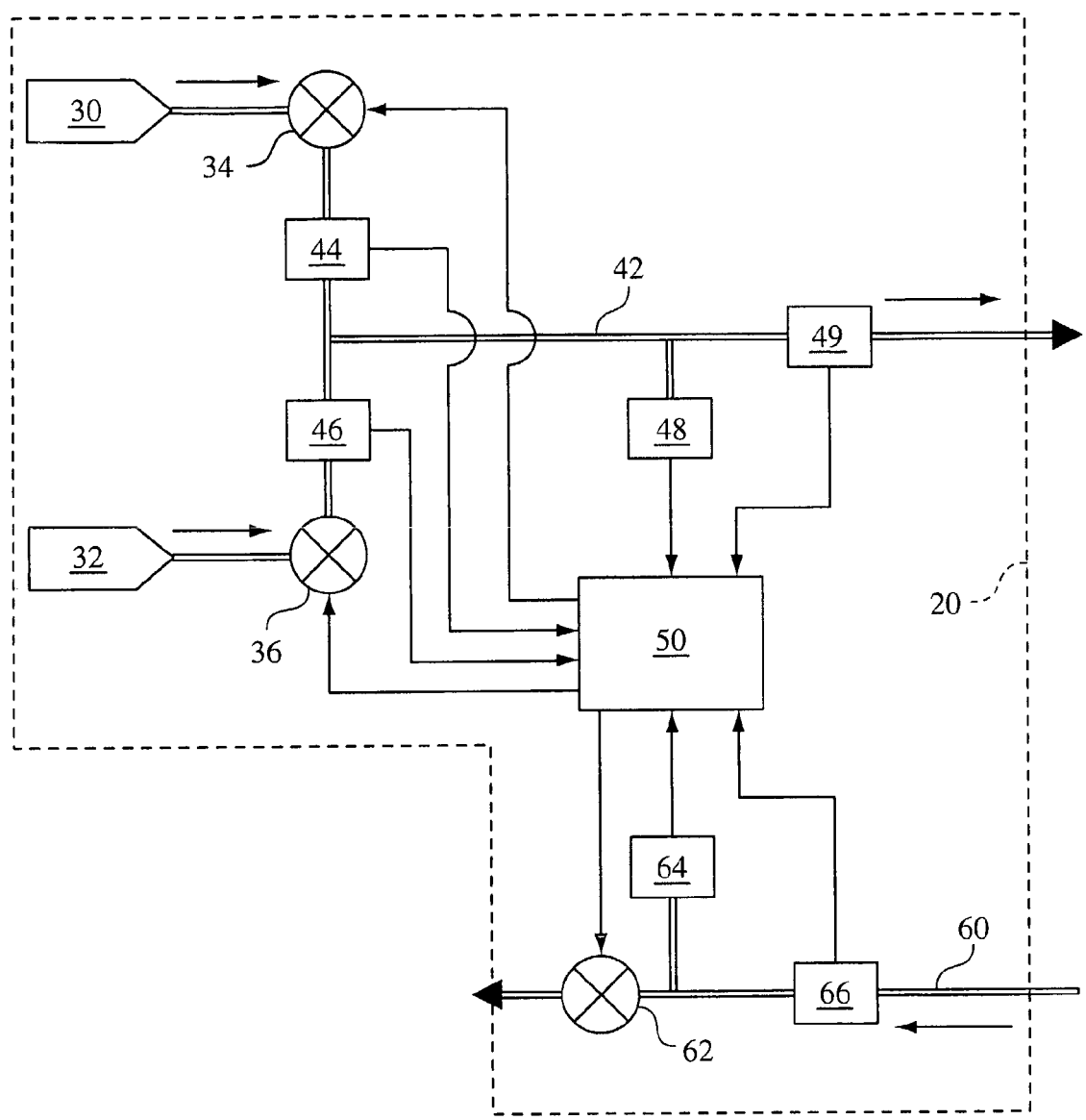
FIG. 1 is a schematic diagram of an exemplary embodiment of a conventional ventilator.
Figure 2:
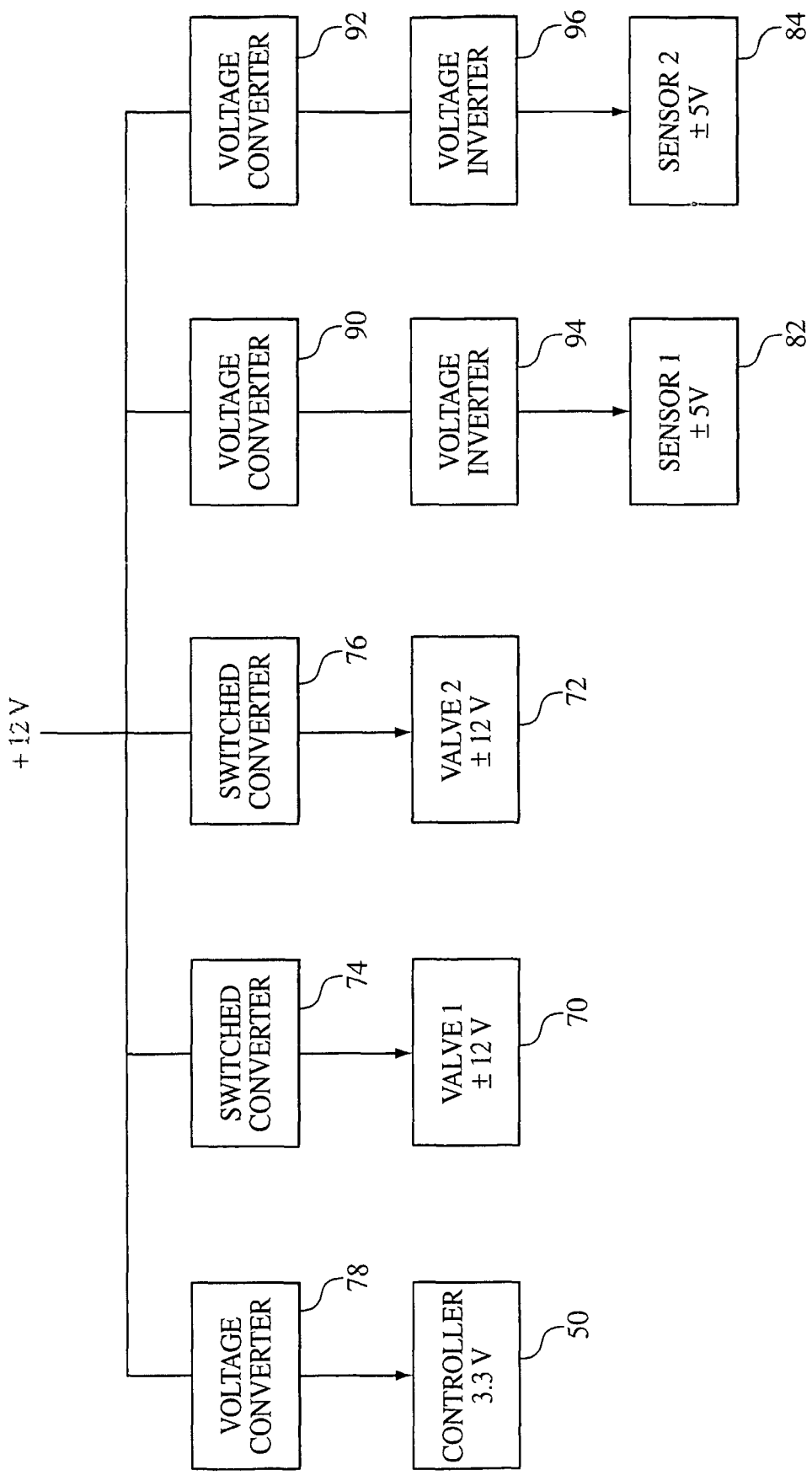
FIG. 2 is a schematic diagram of the power supply system in a conventional ventilator.

The present invention pertains to a system and method for providing power to one or more sensors that are used in a ventilator. Thus, the sensor power supply system of the present invention is used with any conventional ventilator, such as those discussed above and shown in FIGS. 1 and 2. As such, the various features of the ventilator are applicable to the present invention. Thus, a detailed description of the ventilator, which is the operating environment of the sensor driving system is omitted for the sake of brevity. Examples of sensors that are used in a ventilator to which the power supply system of the present invention pertains, include, but are not limited to a pressure sensor, a flow sensor, a temperature sensor, a humidity sensor (absolute or relative), an oxygen concentration sensor, or carbon dioxide sensor, and any other sensor suitable for use in a ventilator, anaesthesia machine, or any other medical device adapted to deliver a flow gas to the airway of the patient.

Many sensors are realised in a Wheatstone bridge configuration. In a typical arrangement, the ends of the bridge are coupled across a voltage sources so that one end of the bridge is coupled to a positive terminal of the voltage source the other end of the bride is coupled to a negative terminal of the voltage source. The present invention provides this power across the Wheatstone bridge, but does so without the need of a negative power supply.

Figure 3:
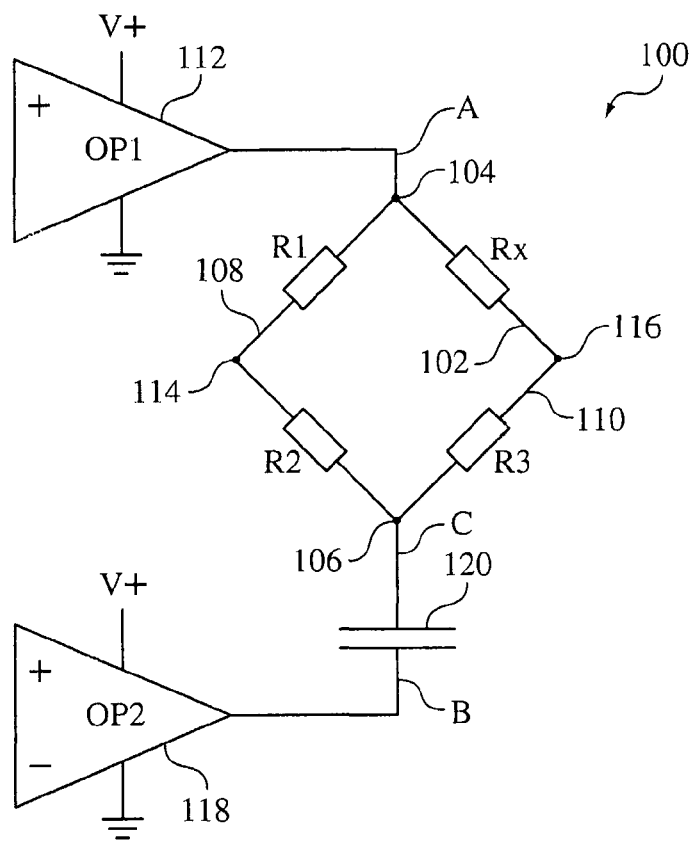
FIG. 3 is a schematic circuit diagram of a first embodiment of sensor circuit that includes a wheatstone bridge according to the principles of the present invention.

Referring now to FIG. 3, a sensor configuration 100 according to the principles of the present invention will now be described. Sensor configuration 100 includes a Wheatstone bridge 102 having a first end 104 and a second end 106. A first leg 108 that includes resistors R1 and R2 extends between first end 104 and second end 106. A second leg 110 that include sensing resistor Rx and resistor R3 extends between the first end and the second end in parallel with the first leg. First end 104 is coupled to a first positive voltage source 112. It should be noted that any of resistors R1 to R3, or any combination of resistors, also can act as sensing elements in the Wheatstone bridge, depending on how the sensor is designed.

The balance of the Wheatstone bridge changes with the parameter being observed by the sensor or sensors. This voltage balance can be monitored at points 114 and 116. Taking the voltage measurement at this location maximizes the measured signal because it provides the greatest voltage drop in the bridge. However, taking the voltage between points 114 and 116 results in a signal that is not referenced to any other point. Thus, this signal is most useful in situations where a relative signal is need. If a referenced signal is needed, the present invention contemplates monitoring the voltage at point 116 relative to ground.

Figure 4:
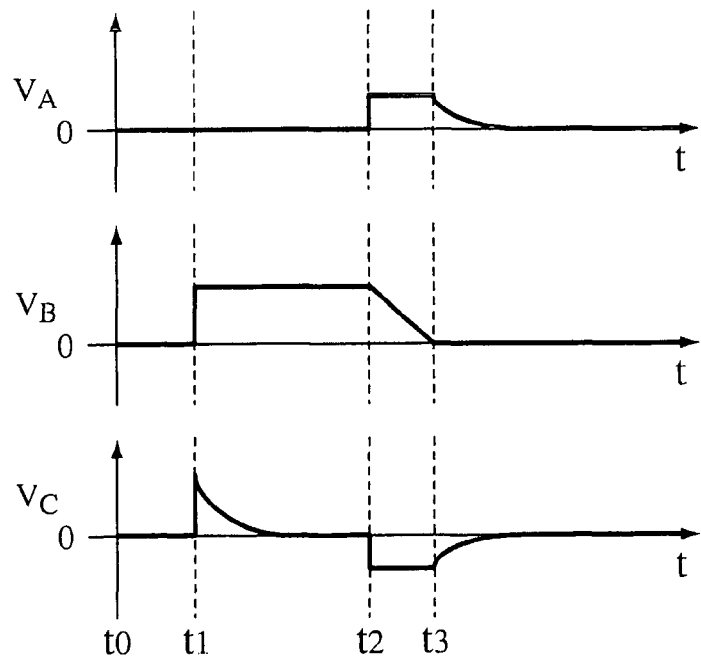
FIG. 4 is a timing diagram illustrates the voltages at various locations in the circuit of FIG. 3 during operation of the power supply circuit.

Sensor configuration 100 includes a capacitor 120 having a first end is coupled to second end 106 of Wheatstone bridge 102. A second positive voltage source 118 is coupled to a second end of the capacitor. First and second positive voltage sources are controlled by a controller, such as controller 50, to provide power to the Wheatstone bridge 102 as illustrated in FIG. 4. More specifically, the first and second positive voltage sources are controlled that power is provided across the bridge only when a measurement is to be taken. At all other times, there is no voltage drop across the bridge, so that no signal is obtained at points 114 or 116. In the illustrated exemplary embodiment, first and second positive voltage sources 112 and 118 are operational amplifier (Op Amps) that are capable of output a controlled positive output. The highest output corresponds to the voltage V+ provided to the Op Amp, and the lowest output corresponds to zero (0) volts.

This is accomplished by actuating first and second positive voltage sources 112 and 118, respectively, such that at time t0, the output of first positive voltage source 112 is kept low, so that the voltage at point A in the circuit of FIG. 3 ($V_A$) is low (0V) and the output of second positive voltage source 118 is kept high. This will charge the capacitor, and when the capacitor is being charged, the charge current ceases, and point B in the circuit of FIG. 3 ($V_B$) is low (0V). At this time, i.e., t0 to t1, capacitor C is charged and the voltage at point C in the circuit of FIG. 3 is also low (0V). Because there is no voltage drop across bridge 102, no measurement, i.e., voltage $V_{114}V_{116}$ or $V_{116}$-$V_{GND}$, can be taken.

At time t1, the output of second positive voltage source 118 is controlled such that a high voltage (V+) is provided. Thus, $V_B$ becomes V+ and capacitor 120 is charged with the voltage V+ during time t1 to t2. By providing a high level to $V_B$ capacitor 120 is charged with a positive voltage, and at the same time, current ceases to the capacitor and through the Wheatstone bridge.

At time t2, the output of second positive voltage source 118 is controlled such that a constant current flows through capacitor 120, and, hence, through the sensing circuit. A typical current is 1.5 mA. This is accomplished by controlling first positive voltage source 112 to provide a high voltage V+ at first end 104 of bridge 102 and allowing the output of second positive voltage source 118 to be regulated towards ground so a constant current flows through the capacitor 120. In other words, the voltage at point B is decreased toward a zero value. This is illustrated by the linear ramp in voltage $V_B$ in FIG. 4 at time t2 to t3. While a linear ramp shape is shown for voltage $V_B$, it can be appreciated that the decrease in voltage can have any shape, and can have a controllable duration.

As a result of these changes at time t2, $V_C$ will become negative (V−). Thus, a voltage V+ to V− is provided across bridge 102 during time interval t2 to t3. In this way the sensor circuit, and, more specifically, the Wheatstone bridge, is fed with a positive and a negative voltage. During this interval, a measurement, i.e., voltage $V_{114}$-$V_{116}$ or $V_{116}$-$V_{GND}$, can be taken. This control maneuver continues until $V_A$ reaches 0V at time t3. Thus, the sensor is effectively enabled during time period t2 to t3 and a sensor reading can be take because the bridge will give an output signal that is in relation to a measured unit, e.g. pressure. At all other times, the sensor is effectively disabled It can be appreciated from the forgoing description that controller controls the first and the second positive voltage sources so as to: (a) disable the sensor by causing the first positive voltage source to provide substantially zero voltage to the first end of the Wheatstone bridge and by causing the second positive voltage source to provide a positive voltage to the second end of the capacitor, and to (b) enable the sensor by causing the first positive voltage source to provide a positive voltage to the first end of the Wheatstone bridge and by causing the second positive voltage source to provide a decreasing voltage towards zero voltage to the second end of the capacitor.

The above technique to provide a negative voltage at second end 106 of the Wheatstone bridge via capacitor 120, obviates the need for a negative supply voltage. This is a significant advantage, because the whole electronics package of the ventilator can be designed with only one inherent supply voltage. In addition, this configuration eliminated that need to switched voltage converters, which, as noted above, tend to induce noise in the power supply system.

Figure 5:
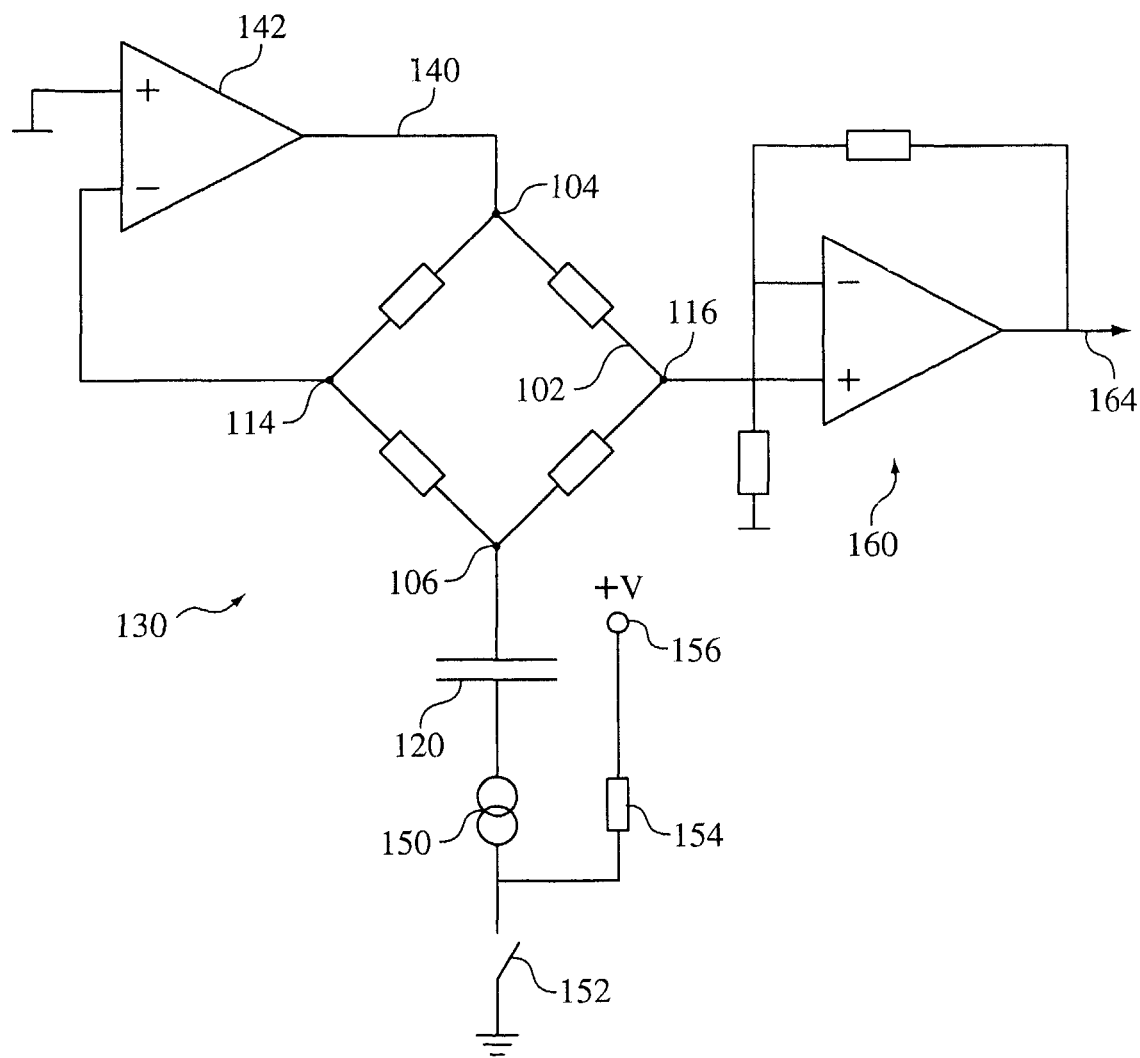
FIG. 5 is a schematic circuit diagram of a second embodiment of sensor circuit according to the principles of the present invention.

A second embodiment of the sensor power supply circuit 130 according to the principles of the present invention is illustrated in FIG. 5. Sensor power supply circuit 130 is generally similar to that of FIG. 3, and is driven in the same way. For example, sensor power supply circuit 130 includes Wheatstone bridge 102 and capacitor 120. However, in this embodiment, a feedback path 140 is provided between a center of the first leg, point 114, and first end 104 of the bridge. An Op Amp 142 is provided in this feedback path. With this feedback the first end 104 of the Wheatstone bridge is driven with a voltage that settles to a level so that center of first leg, point 114, is regulated relative to ground, i.e., point 114 will become a virtual ground.

Sensor power supply circuit 130 also includes a current regulator 150 coupled between the first end of capacitor 120 and switch 152 to ground. Current regulator 150 is activated when a measurement is take so that it feeds the Wheatstone bridge 102 with a constant current. Because a current regulator has a very high output impedance, this current regulation does not conflict with the voltage regulation at center of the first leg of the bride, i.e., the voltage at point 114.

When the sensor power supply circuit 130 is deactivated, the switch 152 is open and the current regulator 150 deactivated, though allowing current to leak through via resistor 154 to power supply 156. In this manner, the first side of the capacitor is fed with a positive voltage.

The output of the bridge is taken at point 116 and is provided to an amplifier circuit 160. This circuit configuration is advantageous in that an output 164 of the amplifier is referenced to ground, and can be calibrated to provide a quantitative measure of the parameter being monitored, rather than merely a relative measurement.

Figure 6:
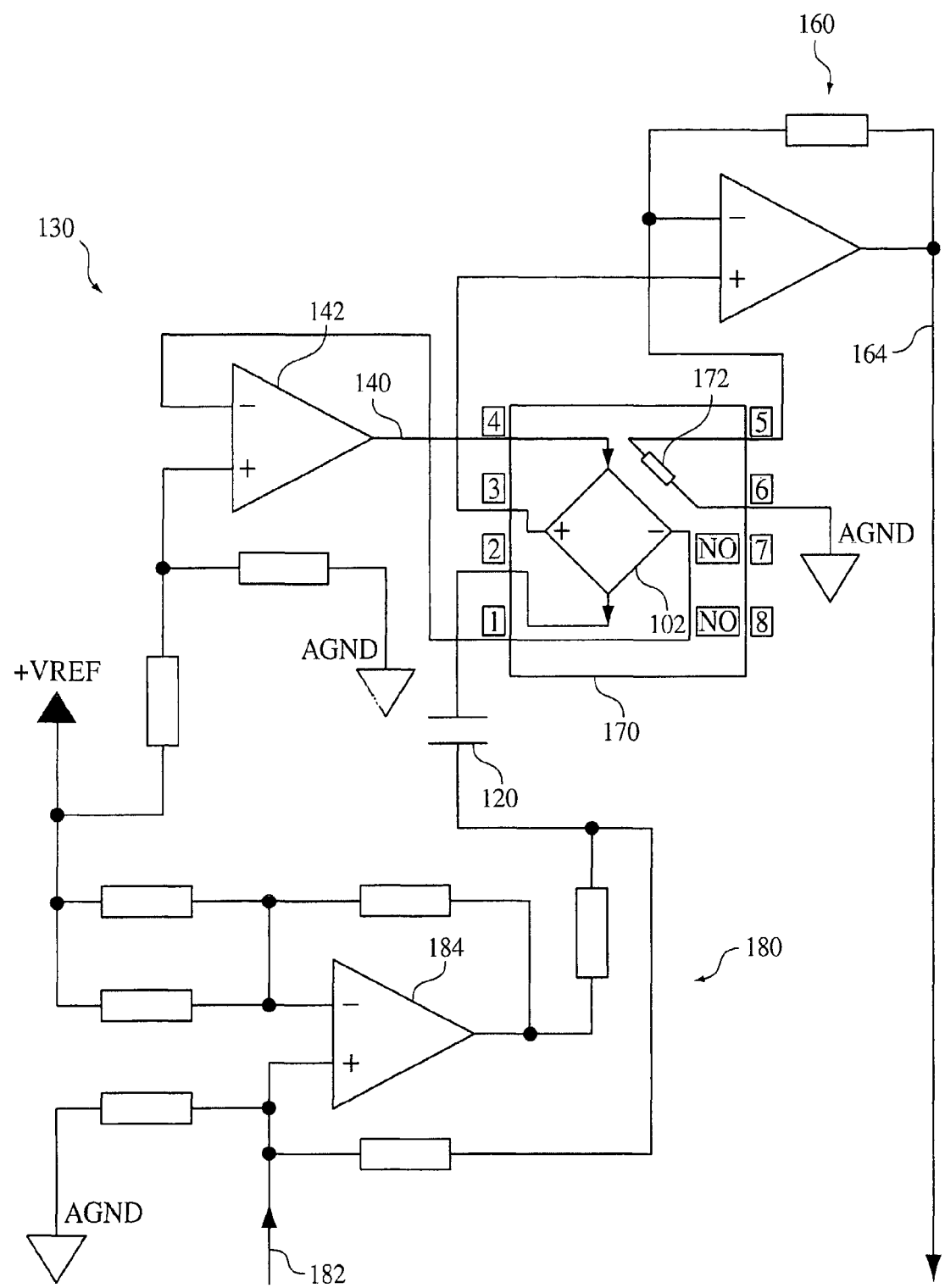
FIG. 6 is a detailed circuit diagram of the sensor circuit of FIG. 5.

FIG. 6 is a more detailed circuit diagram of the implementation of power supply circuit 130 of FIG. 5. In this embodiment, Wheatstone bridge 102 is provided as an integrated circuit 170 with a pressure calibration resistor 172 that settles the gain in the output amplifier 160.

In this embodiment, a constant current circuit 180 is provided to feed the Wheatstone bridge 102 with a constant current. When the sensor power supply circuit 130 is activated, switch 150 is connected to ground, and the current regulator 150 is enabled, feeding a current through the capacitor 120, causing the Wheatstone bridge feeding point 106 to be negative. A signal provided via terminal 182 is provided to Op Amp 184. This signal controls whether the Op Amp 184 output a high level when the current regulator is disabled or a controlled voltage is applied to capacitor 120 when the current regulator is enabled.

Constant current circuit 180 is a Howland current generator, which is well known to those skilled in the art of operational amplifiers. When the signal line 184 is not connected, current regulator 180 is working in its current regulating state. When signal line 180 is connected to ground, amplifier 184 will have a positive fixed output voltage that will charge the second side of capacitor 120 to this voltage level.

It can be appreciated that using the sensor powering technique of the present invention, internal heating-up of the sensor is avoided or at least minimized, because power is only applied to the sensing circuit when a measurement is to be taken. The actuation of the sensor and the reading of the signal from the sensor is made so that one sensor at a time is supplied with power, and only for a short moment, such as several microseconds, while simultaneously reading the measurement signal by means of an electronic data acquisition unit. By only momentarily providing power to a sensor to be read, the negative impact of heating-up of the sensor, such as temperature drift is minimized.

Although the power supply described herein does not use electronic components that create relatively large about of noise, such as DC-DC converters, it is still possible that certain disturbances will be generated or will be present in the power supplied to the bridge, when the sensor is enabled. For example, noise may present in the power supply system as a result of voltage pulses being provided to the electromagnetic valves that are used to control the flow of gas to or from the patient. The present invention seeks to mitigate the adverse affects of this noise by controlling the sequence or pattern by which the sensor is enabled for purpose of taking a sensor measurement. For example, the present invention contemplates enabling the pressure sensors and providing voltage pulses to the valves, in a synchronous fashion, so that the pressure sensor is not enabled at time when a large noise due to power switching is likely to occur. This is analogous to controlling a machine gun to fire through the blades of a spinning propeller in the sensors are controlled so that a measurement is taken only when the valves are at a state of minimal noise.

In addition, the present invention contemplates that the control system enables the sensors in a predetermined pattern, so that any constant noise will always be included in the measurement. These disturbances, hence, become constant in the measured signal and may be subtracted by the measurement system or can be compensated for using any conventional technique. By minimizing noise in the measurement system using the techniques discussed above, a large dynamic range of the measurement system is achieved. Thus, the signal/noise ratio is improved.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A ventilator (20) adapted to deliver a flow of gas to an airway of a patient, wherein the ventilator includes a sensor provided to monitor characteristic associated with the delivery of gas to the patient and a sensor configuration (100, 130) to provide power to the sensor, characterized in that:

the sensor configuration includes a Wheatstone bridge (102) having a first end (104), a second end (106), a first leg (108) extending between the first end and the second end, and a second leg (110) extending between the first end and the second end in parallel with the first leg;

the first end is coupled to a first positive voltage source (112, 142), a capacitor (120) having a first end is coupled to the second end of the Wheatstone bridge;

a second positive voltage source (118, 156, 180) is coupled to a second end of the capacitor; and a controller (50) controls the first and the second positive voltage sources so as to (a) disable the sensor by causing the first positive voltage source to provide substantially zero voltage to the first end of the Wheatstone bridge and by causing the second positive voltage source to provide a positive voltage to the second end of the capacitor, and to (b) enable the sensor by causing the first positive voltage source to provide a positive voltage to the first end of the Wheatstone bridge and by causing the second positive voltage source to provide a decreasing voltage to the second end of the capacitor.

2. The ventilator of claim 1, wherein a feedback path (140) is provided between a center of the first leg and the first end of the Wheatstone bridge.

3. The ventilator of claim 1, wherein an output signal (116) is taken from a center of the second leg of the Wheatstone bridge or between a center of the first leg and the center of the second leg of the Wheatstone bridge.

4. The ventilator of claim 1, further comprising a current regulator (150) coupled between the second end of the Wheatstone bridge and the first end of the capacitor.

5. The ventilator of claim 1, wherein the controller maintains the sensor in the disabled state, enables the sensor only when a measurement it to be taken using the sensor, and causes the sensor to return to the disabled state after the measurement is taken.

6. The ventilator of claim 1, wherein the controller enables the sensor in a routine pattern relative to the actuation of other components of the ventilator.

7. The ventilator of claim 1, wherein the sensor is a pressure sensor, a flow sensor, a temperature sensor, a humidification sensor, or a gas concentration sensor.

8. The ventilator of claim 1, further comprising a plurality of valves for controlling a flow gas, wherein the controller actuates the valves in a routine pattern.

9. A method of providing power to a sensor in a ventilator, wherein the ventilator delivers a flow of gas to an airway of a patient, the sensor monitors a characteristic associated with the delivery of gas to the patient, and a power supply provides power to the sensor, and wherein the sensor configuration includes a Wheatstone bridge having a first end, a second end, a first leg extending between the first end and the second end, and a second leg extending between the first end and the second end in parallel with the first leg, characterized in that the method includes:

provinding a capacitor having a first end is coupled to the second end of the Wheatstone bridge;

disabling the sensor by providing (a) a substantially zero voltage to the first end of the Wheatstone bridge and (b) a positive voltage to the second end of the capacitor; and enabling the sensor by providing (a) a positive voltage to the first end of the Wheatstone bridge and (b) a decreasing voltage to the second end of the capacitor.

10. The method of claim 9, further comprising taking a measurement from the sensor responsive to the sensor being enabled.

11. The method of claim 10, wherein the measurement is a pressure measurement, a flow measurement, a temperature measurement, a humidity measurement, or a gas concentration measurement.

12. The method of claim 9, the sensor is enabled only when a measurement it to be taken using the sensor, otherwise the sensor is disabled.

13. The method of claim 9, the sensor is enabled in a routine pattern.

14. The method of claim 9, further controlling a flow gas by actuating a plurality of valves in a routine pattern.

15. The method of claim 9, further comprising providing a feedback path between a center of the first leg and the first end of the Wheatstone bridge.

* * * * *